United States Patent [19]

Razdan et al.

[11] 4,232,028
[45] Nov. 4, 1980

[54] 17-CYCLOBUTYLMETHYL-4,5α-EPOXY-3-HYDROXY-14-METHOXY-8α-METHYL-MORPHINAN-6-ONE, AND METHOD OF TREATING PAIN WITH IT

[75] Inventors: Raj K. Razdan, Belmont; Anil C. Ghosh, Lexington, both of Mass.

[73] Assignee: Sisa, Incorporated, Cambridge, Mass.

[21] Appl. No.: 49,460

[22] Filed: Jun. 18, 1979

[51] Int. Cl.³ .................. A61K 31/485; C07D 489/08
[52] U.S. Cl. ...................................... 424/260; 546/45
[58] Field of Search ........................... 424/260; 546/45

[56] References Cited

U.S. PATENT DOCUMENTS

| 2,178,010 | 10/1939 | Small et al. | 546/45 |
| 2,694,067 | 11/1954 | Payne et al. | 546/46 |
| 3,162,639 | 12/1964 | Fishman | 546/46 |

FOREIGN PATENT DOCUMENTS

| 913077 | 10/1972 | Canada | 546/45 |

OTHER PUBLICATIONS

Posner, Organic Reactions, vol. 19, pp. 1–113 (1972).

*Primary Examiner*—Donald G. Daus
*Assistant Examiner*—D. Rivers
*Attorney, Agent, or Firm*—Jerome L. Jeffers

[57] ABSTRACT

Disclosed is 17-cyclobutylmethyl-4,5α-epoxy-3-hydroxy-14-methoxy-8α-methylmorphinan-6-one characterized by the formula:

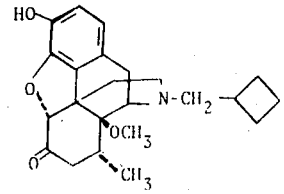

This compound is useful as a mixed analgesic/narcotic antagonist.

6 Claims, No Drawings

17-CYCLOBUTYLMETHYL-4,5α-EPOXY-3-HYDROXY-14-METHOXY-8α-METHYLMORPHINAN-6-ONE, AND METHOD OF TREATING PAIN WITH IT

BACKGROUND OF THE INVENTION

1. Field of the Invention

Morphine is a well known narcotic analgesic having the structural formula:

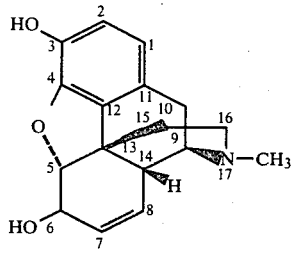

The compound of this invention is structurally related to morphine and is named according to the morphinan system of nomenclature using the morphinan nucleus which is shown below:

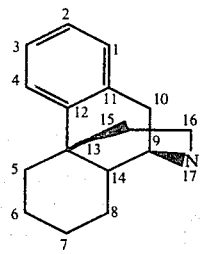

The numbering and stereochemical placement of atoms in the morphinan system is the same as that depicted for morphine. A dashed line is used to represent a covalent bond projecting below the plane of a reference atom while a wedged or heavily accented line signifies a covalent bond above such plane. The compound of this invention has the same stereochemical placement of atoms as depicted for morphine in those positions where the stereochemistry is not depicted by a dashed or wedged line.

Morphine and its structurally related relatives are used primarily as analgesics. While extremely effective for the relief of moderate to severe pain these compounds are narcotic and most possess dependence-inducing ability and produce other side effects such as emesis, constipation, sweating, respiratory depression and myosis which make then less than ideal analgesics. It is impossible to predict, based on structure alone, whether a particular morphine-like compound will act as an analgesic (agonist), a narcotic antagonist or possess a combination of these properties since very minute structural modifications in the molecule result in significant changes in pharmcological activity. A compound with the appropriate profile of analgesic (agonist) and narcotic antagonist actions has potential for treatment of moderate to severe pain without the liability of drug dependence or drug abuse.

2. Prior Art 17-alkyl or cycloalkyl-4,5α-epoxy-3-substituted-14-hydroxy morphinan-6-one compounds corresponding to the formula:

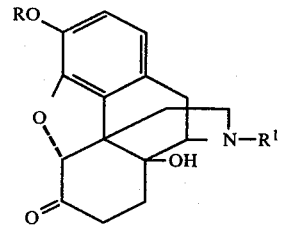

Where R is H or methyl are known. Thus, the foregoing formula represents oxycodone when R and $R^1$ are methyl and oxymorphone when R is H and $R^1$ is methyl. Both of these compounds are known to be useful as narcotic analgesics. The foregoing formula represents naloxone when R is H and $R^1$ is allyl and naltrexone when R is H and $R^1$ is cyclopropylmethyl.

Blumberg et al. disclose in *Narcotic Antagonists* (1974) Pp 33–43 a compound of the formula:

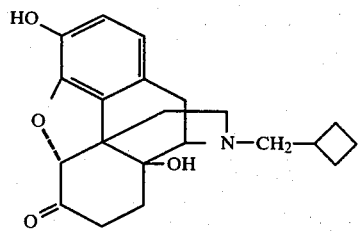

This compound is said to exhibit analgesic activity, having an $ED_{50}$ of 0.39 mg/kg, and narcotic antagonist activity having an $ED_{50}$ of 0.57 mg/kg in counteracting the action of oxymorphone.

The compound of the present invention possesses potent analgesic activity and has demonstrated narcotic antagonist activity.

SUMMARY OF THE INVENTION

The present invention involves 17-cyclobutylmethyl-4,5α-epoxy-3-hydroxy-14-methoxy-8α-methylmorphinan-6-one of the formula:

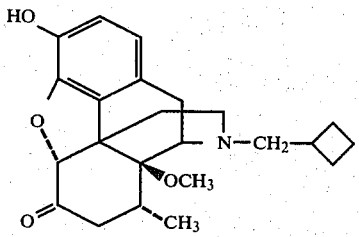

DETAILED DESCRIPTION

The method for the preparation of the compound of the present invention is represented by Scheme I. Referring to Scheme I, 14-methoxycodeinone (1) is reacted with methyllithium in the presence of copper iodide according to the general procedure of Posner, Organic Reactions, Vol 19, P.1, to give the 8α methyl substituted Compound (2). Compound (2) is treated with cyanogen bromide followed by acid hydrolysis to give the nor compound (4) via intermediate (3). The nor compound is then reacted with a cyclobutylmethyl halide to provide Compound (5). Hydrobromic acid is used to convert the methoxy at the 3-position of (5) to the hydroxy group of Compound (6a). Compound (6a) can be converted to its acid addition salt (6b) by treatment with an appropriate acid such as hydrogen chloride.

SCHEME I

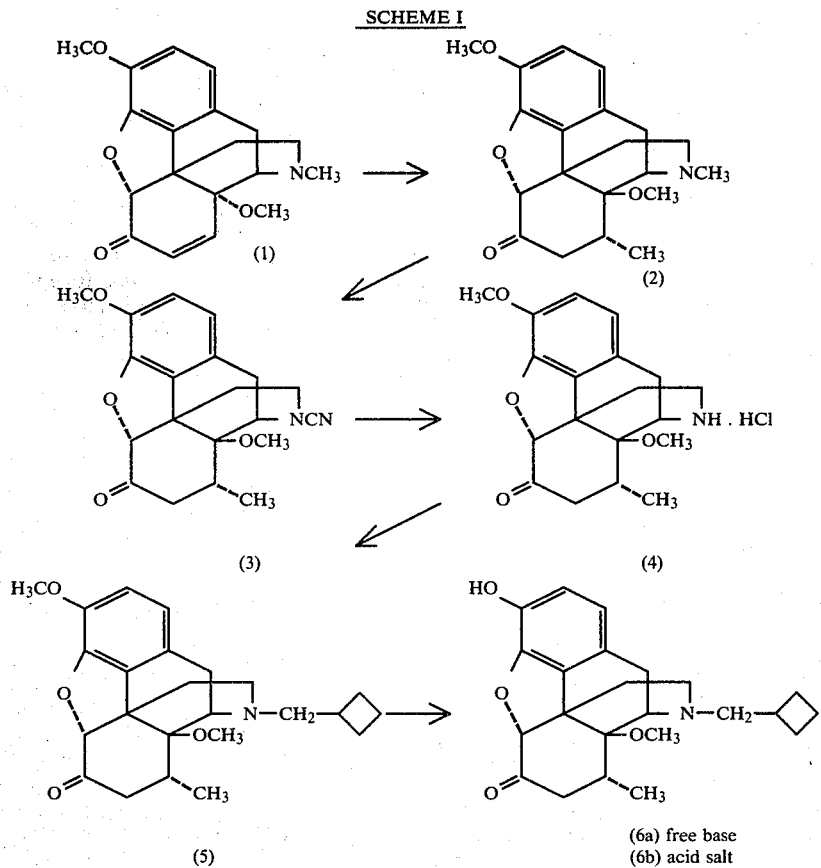

(6a) free base
(6b) acid salt

The preparation and pharmacology of the compound of this invention is further illustrated by the following examples:

EXAMPLE I

14-Methoxycodeinone (1)

To a suspension of sodium hydride (57% oil dispersion, 13.5 g, 0.319 mol) in 30 ml of dimethylformamide under nitrogen was added a solution of 14-hydroxycodeinone [Hauser et al, J. Med. Chem, 17, 1117 (1974)], (25 g, 79.8 mmol) in 450 ml of DMF. The mixture was stirred at room temperature for 1 hour and cooled in an ice bath whereupon methyl iodide (15.5 g, 0.109 mol) was added dropwise and the mixture was allowed to warm up to room temperature. Stirring was continued for another 3 hours and at the end of this period the excess sodium hydride was decomposed very cautiously by the dropwise addition of water. Most of the DMF was removed by distillation in vacuo (oil bath temperature 35°–40° C.) and the residue was taken up in 400 ml of methylene chloride. The organic layer was washed with water (3×100 ml), saturated NaCl solution (2×100 ml) and again with water (3×100 ml). The aqueous layer was re-extracted with methylene chloride (2×300 ml) and the organic extracts were combined. After drying over $MgSO_4$ and filtration, the organic solution was concentrated under reduced pressure to give an orange-brown residue (19.7 g). A solution of the residue in chloroform was passed through a column of Florisil (400 g) and eluted with graded chloroform/benzene mixtures. The fractions containing the desired compound were collected and the product was recrystallized from ethanol to give 13.6 g (50% theory) of the title compound, m.p. 143°–144° C.

Analysis

NMR(CDCl$_3$) δ2.48 (s, 3H, N—CH$_3$), 3.28 (s, 3H, C$_{14}$—OCH$_3$), 3.83 (s, 3H, C$_3$—OCH$_3$), 4.73 (s, 1H, C$_5$—H) and 6.43–6.80 (m, 2H, aromatics). IR (CHCl$_3$) $v_{max}$ 1683 cm$^{-1}$ (>C=O).

Anal. Calcd. for $C_{19}H_{21}NO_4$: C, 69.70; H, 6.47; N, 4.28. Found: C, 69.73; H, 6.46; N, 4.17.

EXAMPLE II

3,14-Dimethoxy-8α,17-dimethyl-4,5α-epoxymorphinan-6-one (2)

To a suspension of copper iodide (10.49 g, 57.3 mmol) in dry tetrahydrofuran (50 ml) and ether (50 ml), cooled in an ice bath, methyllithium (60 ml of a 1.84 M solution, 0.11 mmol) was added under a nitrogen atmosphere. After 10 minutes, a solution of 14-methoxycodeinone (7,8-didehydro-3,14-dimethoxy-4,5α-epoxy-17-methylmorphinan-6-one) prepared as described in Example I (15.0 g, 45.8 mmol) in tetrahydrofuran (300 ml) was added and the mixture was stirred for 3 hours. At the end of this period a saturated solution of ammonium chloride (200 ml) was added slowly followed by a 20%

NaOH solution until the mixture was basic. The aqueous layer was separated and extracted with ethyl acetate (3×100 ml). The organic extracts were combined, washed once with water (100 ml), dried over MgSO$_4$, filtered and evaporated to give 13.6 g of the crude title compound. This material was recrystallized from ethanol to give 8.0 g (51%) of product in the form of colorless needles, mp 204°–205° C.

Analysis

NMR (CDCl$_3$) δ0.52 (d, J=7 Hz, 3H, C$_8$—CH$_3$), 2.4 (s, 3H, N—CH$_3$), 3.4 (s, 3H, C$_{14}$—OCH$_3$), 3.97 (s, 3H, C$_3$—OCH), 4.68 (s, 1H, C$_5$—H) and 6.52–6.83 (m, 2H, aromatics). IR (CHCl$_3$) γ$_{max}$ 1723 cm$^{-1}$ (>C=O).

Anal. Calcd. for C$_{20}$H$_{25}$NO$_4$: C, 69.95; H, 7.34; N, 4.08. Found: C, 69.99; H, 7.26; N, 3.97.

EXAMPLE III

17-Cyano-3,14-dimethoxy-4,5α-epoxy-8α-methylmorphinan-6-one (3)

A solution of 3,14-dimethoxy-8α,17-dimethyl-4,5α-epoxymorphinan-6-one (2) (0.89 g, 2.59 mmol) in a mixture of 25 milliliters CHCl$_3$/25 milliliters CH$_2$Cl$_2$ was treated with anhydrous Na$_2$CO$_3$ (1.6 g, 15.09 mmol), followed by cyanogen bromide (1.6 g, 15.10 mmol). The reaction mixture was refluxed overnight with stirring while being kept under a nitrogen atmosphere. The sodium carbonate was removed by filtration and the filtrate concentrated under reduced pressure to give 0.89 g (97%) of the title compound as a brownish solid. The product, which showed only a single spot on tlc, was used without further purification.

Analysis

NMR (CDCl$_3$) δ0.43 (d, J=6 Hz, 3H, C$_8$—CH$_3$), 3.47 (s, 3H, C$_{14}$—OCH$_3$), 3.93 (s, 3H, C$_3$—OCH$_3$), 4.67 (s, 1H, C$_5$—H) and 6.53–6.87 (m, 3H, aromatics). IR (CHCl$_3$) γ$_{max}$ 1728 cm$^{-1}$ (>C=O) and 2240 cm$^{-1}$ (N—C≡N).

EXAMPLE IV 3,14-Dimethoxy-4,5α-epoxy-8α-methylmorphinan-6-one Hydrochloride (4)

17-Cyano-3,14-dimethoxy-4,5α-epoxy-8α-methylmorphinan-6-one (3) (6.0 g, 16.9 mmol) was combined with 250 ml of 2N HCl and refluxed under a nitrogen atmosphere for 3 hours. The contents of the reaction flask were concentrated under reduced pressure to give 6.1 g (99% theory) of a brownish solid which was dried and used without further purification.

Analysis

NMR (D$_2$O) δ0.43 (d, J=7 Hz, 3H, C$_8$—CH$_3$), 3.53 (s, 3H, C$_{14}$—OCH$_3$), 3.93 (s, 3H, C$_3$—OCH$_3$), 6.73–7.13 (m, 2H, aromatics).

EXAMPLE V

17-Cyclobutylmethyl-3,14-dimethoxy-4,5α-epoxy-8α-methylmorphinan-6-one (5)

A mixture of 3,14-dimethoxy-4,5α-epoxy-8α-methylmorphinan-6-one hydrochloride (4) (3.4 g, 9.29 mmol), cyclobutylmethyl bromide (3.4 g, 22.8 mmol), sodium bicarbonate (5.0 g, 59.5 mmol) and 100 milliliters of dimethylformamide was heated at 105° to 100° C. while being stirred and maintained under a nitrogen atmosphere. The reaction mixture was heated for 18 hours, after which the inorganic material was removed by filtration and the filter cake was washed twice with dimethylformamide (100 ml). The filtrate and washings were combined and distilled under high vacuum (bath temperatures 35° C.) and the material which remained was taken up with ethyl acetate (300 ml)/H$_2$O (80 ml) and made basic by the addition of saturated sodium bicarbonate solution. After separating the organic layer, the aqueous phase was re-extracted with ethyl acetate (2×150 ml). The combined ethyl acetate extracts were dried over MgSO$_4$, filtered and concentrated under reduced pressure to give 3.1 g (84% theory) of the crude desired product. This material was purified by chromatography on silica gel using benzene followed by 50:50 benzene/chloroform, chloroform and graded (2% to 50%) methanol/chloroform mixtures. Those fractions containing pure product were combined and evaporated to give 1.39 g (38% theory) of the desired compound as a foamy solid. A portion of the product was converted to the hydrochloride salt by treatment with ethereal hydrogen chloride.

Analysis

NMR (CDCl$_3$) δ0.5 (d, J=8 Hz, 3H, C$_8$—CH$_3$), 3.37 (s, 3H, C$_{14}$—OCH$_3$), 3.93 (s, 3H, C$_3$—OCH$_3$), 4.7 (s, 1H, C$_5$—H) and 6.47–6.87 (m, 2H, aromatics). IR (CHCl$_3$) γ$_{max}$1722 cm$^{-1}$ (>C=O).

Anal. Calcd. for C$_{24}$H$_{32}$NO$_4$Cl: C, 66.42; H, 7.43; N, 3.23; Cl, 8.17. Found: C, 66.33; H, 7.42; N, 3.30; Cl, 8.07.

EXAMPLE VI

17-Cyclobutylmethyl-4,5α-epoxy-3-hydroxy-14-methoxy-8α-methylmorphinan-6-one (6a) Hydrochloride (6b) (TR-5162)

A mixture of 17-cyclobutylmethyl-3,14-dimethoxy-4,5α-epoxy-8α-methylmorphinan-6-one (5) (1.0 g, 2.51 mmol) and 20 milliliters of hydrobromic acid (48%) was heated at reflux for 20 minutes. The solution was concentrated under reduced pressure and the resulting solid was dissolved in 100 milliliters of ethyl acetate whereupon dilute NH$_4$OH was added until the solution was basic. The organic layer was separated, washed with a saturated NaCl solution, dried over MgSO$_4$ and filtered. Evaporation of the solvent under reduced pressure gave an oily solid which was purified by column chromatography on silica gel. The column was eluted with 50:50 benzene/CHCl$_3$, followed by CHCl$_3$ and graded with (2% to 100%) methanol/chloroform mixtures. Conversion to the HCl salt by treatment with ethereal HCl gave 0.192 g (29% theory) of the title compound as a foamy solid.

Analysis

NMR (CDCl$_3$+CD$_3$OD) δ0.47 (d, J=7 Hz, 3H, C$_8$—CH$_3$), 3.38 (s, 3H, C$_{14}$—OCH$_3$), 3.4 (s, 3H, C$_3$—OCH$_3$), 4.73 (s, 1H, C$_5$—H) and 6.47–6.9 (m, 2H, aromatics).

Anal. Calcd. for C$_{23}$H$_{30}$NO$_4$Cl: C, 65.78; H, 7.20; N, 3.33; Cl, 8.44. Found; C, 65.67; H, 7.30; N, 3.34; Cl, 8.54.

PHARMACOLOGICAL EVALUATION

The compound whose preparation is disclosed in the foregoing example was screened to determine the following biological activities:

(A) Analgesic effects upon mice (acetic acid writhing test).

(B) Narcotic antagonist activity in rats (modified rat tail flick test).

TEST A

Acetic Acid Mouse Writhing Test

The analgesic effect of the test compound was determined in mice by use of the acetic acid writhing test described by B. J. R. Whittle, Brit. J. Pharmacol., 22: 296 (1964). In this test at least three groups of 5 male CD-1 mice each were given subcutaneous doses of the test drug dissolved in distilled water. In all cases 0.4 milliliters of a 0.5% V/V acetic acid in distilled water solution was administered intraperitoneally 15 minutes post drug. The number of writhes in a 20 minute interval beginning 5 minutes after the acetic acid injection were determined and compared with the number of writhes in a control group which had received only acetic acid.

Percent inhibition of writhing was calculated as:

$$\% \text{ inhibition} = \left[ \frac{\text{No. Control Writhes} - \text{No. Treated Writhes}}{\text{No. Control Writhes}} \right]$$

The $ED_{50}$ dose, i.e., the dose required to reduce the number of writhes by 50%, was determined graphically from a plot of % inhibition as a probit versus log dose. Confidence limits of 95% were calculated on the basis of those results falling in the range 16–84% inhibition. See Litchfield, J. T. and Wilcoxon, F., J. Pharmacol. Exp. Ther., 96, 99–113 (1949).

TEST B

Evaluation of Narcotic Antagonist Activity

The narcotic antagonist effect of the test compound was determined by a modification of the rat tail flick procedure of Harris and Pierson (J. Pharmacol. Exp. Ther., 143:141 [1964]).

Male albino Wistar rats (100–120 g) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp is used to adjust the intensity of the light falling on the tail of the rat such that the rat's control reaction time is from two to four seconds. Animals with a control reaction time outside this range are rejected. The rheostat adjustment is made only if a significant proportion (more than 2 out of every 10 rats) of the reaction times are outside the range of two to four seconds. Groups of 5 rats were used, and two control times were determined at 60 and 30 minutes prior to subcutaneous injection of the drug. A ten second cut-off time is employed; if the rat does not flick its tail in 10 seconds it is removed from the heat source.

Thirty minutes after the last control run the test drug was given intraperitoneally. This was followed ten minutes later by an $ED_{80}$ dose of morphine subcutaneously. The animals were retested at 20 minutes after the morphine injection. Control animals were given vehicle and morphine only. The data were calculated as follows:

$$\% \text{ Effect } (E) = \frac{\{MRT^* \text{(Treated)} - MRT \text{(Control)}\} \times 100}{10 - MRT \text{(Control)}}$$

$$\% \text{ Antagonism} = \frac{\{E \text{(morphine control)} - E \text{(Drug treated)}\} \times 100}{E \text{(morphine control)}}$$

*MRT is defined as mean reaction time.

The data were plotted on log-probit paper and $AD_{50}$ values, i.e., the dose required to inhibit the effect of morphine by 50% within 95% confidence limits, were determined by the method of Litchfield and Wilcoxon.

Using the foregoing procedures, the compound of the present invention was determined to have an $ED_{50}$ of 0.04 mg/kg and an $AD_{50}$ of 5.6 mg/kg. Based on these results it can be seen that the compound is a mixed analgesic/narcotic antagonist exhibiting very potent analgesic activity.

Morphinan type compounds which possess both agonist and narcotic antagonist activity are of special interest because they can be used to treat pain without the liability of drug dependence in an individual to whom they are administered. The term "individual" is used herein to mean a human being or an experimental animal that is a model for a human being. The dose to be administered to achieve the desired result, i.e., the effective dose, may vary from individual to individual but is readily determined by one skilled in the art without undue experimentation.

The compound of the present invention forms pharmacologically acceptable addition salts with organic and inorganic acids. Typical acid addition salts are the tartrate, hydrobromide, hydrochloride and maleate. The hydrochloride is preferred. The compound of the present invention may be administered by known, conventional methods of therapeutic administration such as intravenous, parenteral, buccal, rectal or oral. Dose forms for the administration of this compound can be prepared by methods recognized in the pharmaceutical sciences.

What is claimed is:

1. 17-cyclbutylmethyl-4,5α-epoxy-3-hydroxy-14-methoxy-8α-methylmorphinan-6-one characterized by the formula:

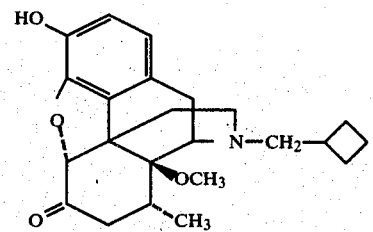

2. The compound defined by claim 1 in the form of its pharmacologically acceptable acid addition salt.

3. The hydrochloric acid addition salt of the compound defined by claim 1.

4. A therapeutic method for treating pain without liability of drug dependence in an individual for whom such therapy is indicated which method comprises administering an effective analgesic amount of a compound corresponding to the structural formula:

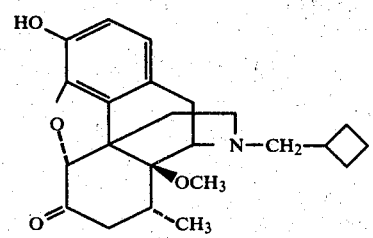

5. The method of claim 4 wherein the compound is administered in the form of its pharmacologically acceptable acid addition salt.

6. The method of claim 4 wherein the compound is administered in the form of its hydrochloric acid addition salt.